United States Patent [19]
Hill et al.

[11] 4,024,396
[45] May 17, 1977

[54] METHOD AND APPARATUS FOR DETECTION UTILIZING RYDBERG LEVELS

[75] Inventors: Robert M. Hill; Thomas F. Gallagher, both of Palo Alto, Calif.

[73] Assignee: Stanford Research Institute, Menlo Park, Calif.

[22] Filed: May 10, 1976

[21] Appl. No.: 684,859

[52] U.S. Cl. .............................. 250/338; 250/330; 356/75; 356/85
[51] Int. Cl.² .......................................... G01J 3/30
[58] Field of Search .......... 250/338, 330, 340, 352; 356/75, 85, 86

[56] References Cited
UNITED STATES PATENTS

| | | | |
|---|---|---|---|
| 3,675,018 | 7/1972 | Paul | 250/338 |
| 3,764,807 | 10/1973 | Pollack | 250/330 |
| 3,802,777 | 4/1974 | Regnier et al. | 356/75 |
| 3,914,618 | 10/1975 | Harris | 250/330 X |

*Primary Examiner*—Archie R. Borchelt
*Attorney, Agent, or Firm*—Victor R. Beckman

[57] ABSTRACT

Highly sensitive method and apparatus for photon detection in the microwave and infrared regions of the electromagnetic energy spectrum are shown in which atoms of a material in the vapor state are excited to a first Rydberg energy level by use of radiation from one or more laser beams. The Rydberg excited material is subjected to the low energy radiation to be detected to induce therein an allowed electric dipole transition from said first to a second Rydberg energy level of the same or quite similar principal quantum number. Spontaneous high energy emission as a result of a distinctive radiative transition from said second Rydberg energy level is detected independently of other radiative transitions by conventional photodetector means such as a photomultiplier operable within the optical spectrum. The photomultiplier output provides a measure of said radiation to be detected. Tuning may be provided by the application of a magnetic field of selected strength to the atoms for Zeeman splitting of the first and second Rydberg energy levels. Also, for photon detection over a range of frequencies, a space or time varying magnetic field may be employed together with suitable photodetection means.

20 Claims, 4 Drawing Figures

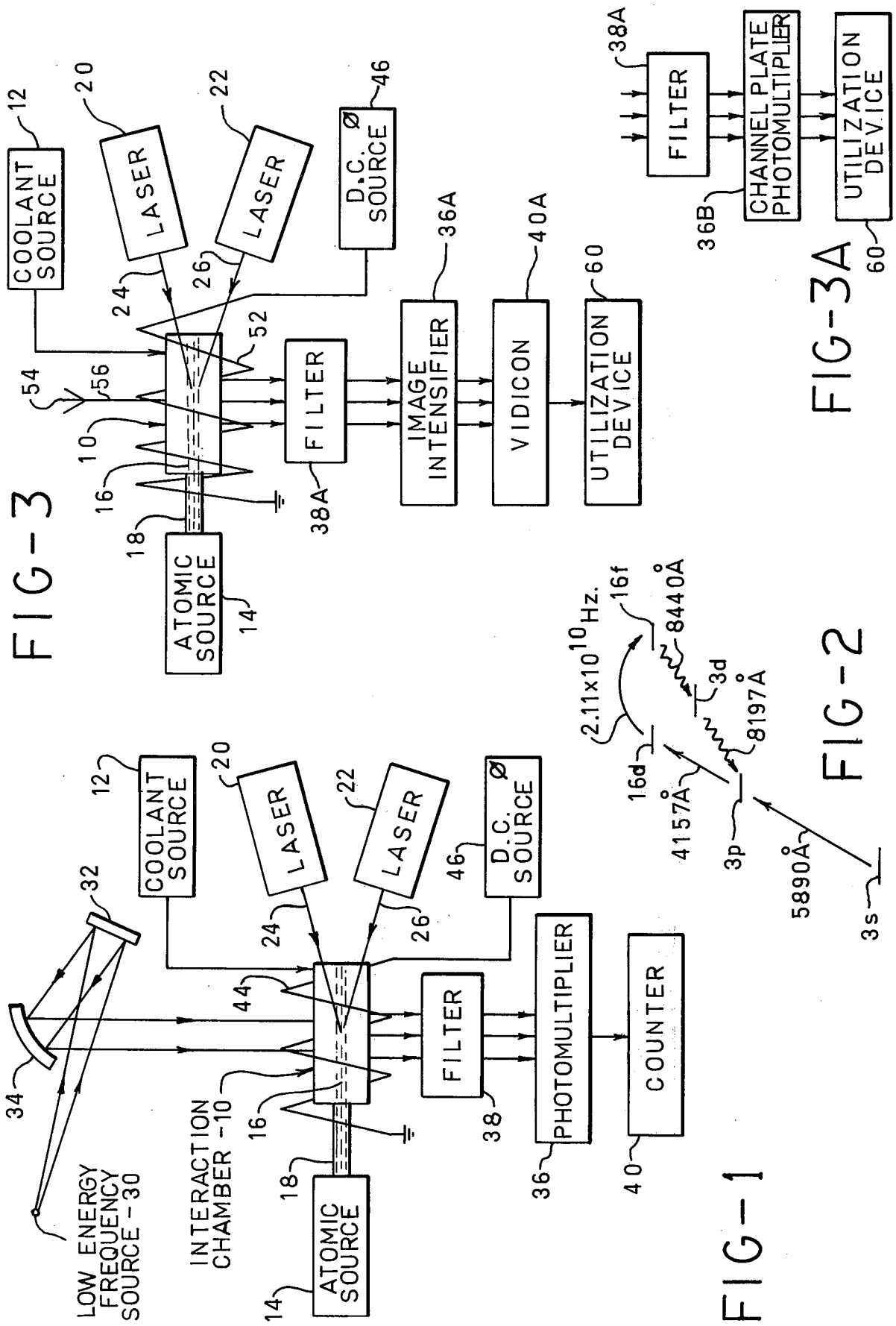

METHOD AND APPARATUS FOR DETECTION UTILIZING RYDBERG LEVELS

ORIGIN OF INVENTION

The invention herein described was made in the course of or under a contract or subcontract thereunder, with the Department of the Air Force.

BACKGROUND OF INVENTION

Numerous instruments for the measurement of radiation within the microwave and infrared frequency range of the electromagnetic radiation spectrum are known. Infrared responsive instruments include transducers such as thermocouples, Golay cells, photoconductors and the like, for transforming said infrared energy to a more directly useful form. Such transducers, however, are inefficient and are of low sensitivity and large bandwidth in the relatively low energy infrared frequency range. In the microwave region, paramagnetic amplifiers often are used for amplification of low microwave signals for subsequent detection. The sensitivity of such prior art microwave and infrared detecting arrangements does not approach that obtained with the present invention in which direct counting of photons in the infrared and microwave frequency range is possible.

SUMMARY OF INVENTION

An object of this invention is the provision of extremely sensitive method and apparatus for detection of electromagnetic energy in the low energy microwave and infrared range.

An object of this invention is the provision of detecting method and apparatus for low energy radiation, in the microwave and infrared region, which are substantially as sensitive as prior art detecting method and apparatus operable in the relatively higher energy, visible, region of the spectrum.

The above and other objects and advantages of this invention are achieved by resonant excitation of atoms of a material in the vapor state to a first Rydberg energy level by laser excitation. The excited atoms are exposed to the relatively low energy radiation to be detected, photons in the range of say $10^{-6}$ to $10^{-2}$ eV, to induce therein allowed electric dipole transitions from said first Rydberg energy level to a second Rydberg energy level in the same of nearby principal quantum state. From such second Rydberg energy level spontaneous energy transition to a lower principal quantum level takes place by the emission of radiation at a higher energy level than that of the microwave or infrared energy to be detected. Decay along one path produces high energy radiation on the order of leV which is unique to the process. After passage through suitable filter means to isolate the unique high energy radiation, the radiation is readily detected by use of photodetector means such as a photomultiplier tube or the like, which is highly sensitive to said higher energy level radiation. The novel arrangement comprises in effect, an efficient up-converter for producing readily detected photons in the 1-2 eV energy range for each photon in the $10^{-6}$ to $10^{-2}$ eV range which is absorbed. Tuning may be provided by subjecting the reaction to a magnetic field for Zeeman splitting of the first and second Rydberg energy levels.

BRIEF DESCRIPTION OF DRAWINGS

FIG. 1 is a simplified diagrammatic view of apparatus for low energy level photon detection embodying this invention, FIG. 2 is an energy level diagram for an atom of material which may be used in the invention and showing transitions involved in the operation of the photon detection method and apparatus of this invention, FIG. 3 is a simplified diagrammatic view of a modified form of apparatus employing a spatially inhomogeneous magnetic field for photon detection over a range of frequencies, and FIG. 3A shows a channel plate photomultiplier for use in the arrangement of FIG. 3.

Reference first is made to FIG. 1 wherein photon detecting means utilizing Rydberg energy levels of atoms is shown for use in low energy photon detection in, say, the microwave and infrared range of the electromagnetic spectrum. The detector comprises an interaction chamber, or cell, 10 which may be cooled with a low temperature coolant such as liquid nitrogen or helium supplied thereto from a source of coolant 12. The chamber also is supplied with atoms of any suitable material, such as sodium, from an atomic source 14 comprising an oven containing the material to be vaporized. If desired, an atomic beam 16 of the material may be provided to the chamber by passage of the atoms through a tube 18 from the oven to the chamber. Means are provided for pumping atoms within the interaction chamber to a first Rydberg energy level. For purposes of illustration such pumping means are shown comprising first and second lasers 20 and 22 having beams 24 and 26, respectively, which illuminate a common atomic beam volume. The beams enter the interaction chamber through windows, not shown, in a chamber wall and intersect at a location along the atomic beam. Ambient light is prevented from entering the chamber to avoid detection thereof in the output. Illumination 24 by the one laser 20 optically pumps atoms of the material to an intermediate excited state, and a second resonant excitation of the excited atoms by the illuminating beam 26 from laser 22 pumps the excited atoms to a first Rydberg energy state of high principal quantum number. Excitation to a selected Rydberg energy state is not limited to the illustrated two photon excitation. Single photon and three or more resonant excitation means also are contemplated.

In accordance with the present invention highly excited atoms within the interaction chamber are exposed to the low energy radiation to be detected in the microwave or infrared range to effect an allowed electric dipole transition from said first Rydberg energy state to a second Rydberg energy state of the same or nearby principal quantum number. For purposes of illustration a source 30 of electromagnetic radiation in the infrared range is shown from which source radiation is directed onto highly excited atoms in the interaction chamber through a window, not shown, by use of plane and curved mirrors 32 and 34, respectively. For use in the microwave region an antenna and waveguide arrangement, such as shown in FIG. 3, could be employed as a radiation collector. Atoms in said first Rydberg energy state are excited to a second Rydberg energy state at the same or nearby principal quantum number by absorption of photons of microwave or infrared radiation of a particular energy. A decay path of an atom from the second Rydberg energy level includes the production of an optical photon which is approximately $10^2$ to $10^6$ times more energetic than the low energy microwave or infrared radiation to be detected. Furthermore, such high energy photon produced by such spontaneous emission in decay from the second Rydberg energy level is unique to the method. The wavelength produced can only result from such spontaneous emission, and the second Rydberg energy state can only be reached by absorption of the microwave or infrared photons of particular energy.

The high energy level photons of unique frequency are sensed by photosensing means 36 comprising, for example, a photomultiplier. Filter means 38 are included between the photomultiplier 36 and interaction chamber to restrict the observed photons to the desired frequency, or frequency range, without viewing other photons emanating from the chamber, including those produced by decay along other paths. Photomultipliers which are highly sensitive in the optical range are available for use with the present invention. The output from the photomultiplier is supplied to a utilization circuit 40 such as a counter, current meter, or the like, for display, recording, or other use of the photon count.

For a better understanding of the novel photon detection method, a brief consideration of atoms in the high lying or Rydberg energy states is in order. The behavior of such atoms is quite different from that of atoms in the ground or lower excited states. The different behavior stems, primarily, from the fact that in the Rydberg state electrons are in a large, loosely bound, orbit. For example, in $n=11, l=3$, the average value of the orbital radius is 100A, while the binding energy is only 0.12 eV. Consequently, atoms in Rydberg states are highly polarizable and exhibit large cross sections for collision processes. Additionally, the large orbit of the electron has a poor overlap with the radial wave functions of the lower states, giving rise to long radiative lifetime. An examination of Table I, below, illustrates these properties.

TABLE I

ATOMIC RYDBERG LEVEL BEHAVIOR
WITH PRINCIPAL QUANTUM NUMBER n

| | |
|---|---|
| Energy Level (below ionization potential) | $1/n^2$ |
| Separation between energy levels | $1/n^3$ |
| Electron Orbital diameter | $n^2$ |
| Transition Probability (neighboring levels) | $n^4$ |
| Polarizability | $n^7$ |

From Table I it is seen that the energy levels (distance from the ionization potential) scale as $1/n^2$ while the difference between energy levels scales as $1/n^3$. As a result, the energy levels are much closer together as $n$ increases. The orbital diameter scales as the square of the quantum number. Also, as seen from Table I, the probability of absorption of the low energy photon by the high Rydberg state atom for transition to the second Rydberg level varies as $n^4$, and polarizability of the atom varies as $n^7$.

In addition to the above, atoms such as Na differ from hydrogen atoms in that for each principal quantum number $n$ the levels of different orbital angular momentum $l$ are non-degenerate, scaling as $(n - \epsilon_l)^{-2}$ where $\epsilon_l$ is the quantum defect for a particular $l$ and is substantially independent of $n$. The frequency difference between neighboring energy levels which scales as $1/n^3$ as noted from Table I, substantially is defined as follows:

$$\text{Frequency} = 2R\left(\frac{1}{(n_1 - \epsilon_l)^2} - \frac{1}{(n_2 - \epsilon_{l'})^2}\right)$$

equation (1)

where R is the Rydberg constant which equals $3.29 \times 10^{15}$ $H_z$. Table 2, below, gives values for $\epsilon_l$ for the $s,p,d,f$ and $g$ levels in Na.

TABLE 2

| l | s | p | d | f | g |
|---|---|---|---|---|---|
| Quantum Defect ($\epsilon_l$) | 1.35 | 0.855 | 0.0142 | 0.0013 | 0.0004 |

Employing quantum defect values from Table 2 in equation (1), approximate values of Rydberg level transitions for Na may be calculated, and a number of such transitions is contained in Table 3, below.

TABLE 3

FREQUENCY DIFFERENCE BETWEEN NEIGHBORING LEVELS, Na

| n | Δf s-p | Δf(n+1)p-nd | Δf d-f |
|---|---|---|---|
| 12 | $2.52 \times 10^{12}$ Hz | $5.96 \times 10^{11}$ Hz | $4.99 \times 10^{10}$ Hz |
| 13 | $1.93 \times 10^{12}$ | $4.65 \times 10^{11}$ | $3.92 \times 10^{10}$ |
| 14 | $1.52 \times 10^{12}$ | $3.76 \times 10^{11}$ | $3.15 \times 10^{10}$ |
| 15 | $1.21 \times 10^{12}$ | $3.06 \times 10^{11}$ | $2.56 \times 10^{10}$ |
| 16 | $9.86 \times 10^{11}$ | $2.52 \times 10^{11}$ | $2.11 \times 10^{10}$ |
| 17 | $8.11 \times 10^{11}$ | $2.10 \times 10^{11}$ | $1.76 \times 10^{10}$ |
| 18 | $6.75 \times 10^{11}$ | $1.77 \times 10^{11}$ | $1.49 \times 10^{10}$ |
| 19 | $5.68 \times 10^{11}$ | $1.51 \times 10^{11}$ | $1.26 \times 10^{10}$ |
| 20 | $4.83 \times 10^{11}$ | $1.29 \times 10^{11}$ | $1.08 \times 10^{10}$ |

Relevant energy levels employed in a system which has been built and tested are shown in FIG. 2 to which reference now also is made. Sodium in the vapor state, as provided by atomic source 14, is exposed to illumination from the laser 20 operating at a wavelength of substantially 5890 A for resonant excitation of ground level atoms at the $3s$ state to the $3p$ energy level. By illumination from the second laser 22 operating at a wavelength of substantially 4157 A, the excited atoms are pumped to a high level i.e. to the $16d$ Rydberg energy level. From Table 3 it will be seen that there exists an allowed electric dipole transition at the microwave level of $2.11 \times 10^{10}$ $H_z$ for sodium atoms between the $d$ and $f$ levels at the principal quantum number 16. The absorption cross section of such low frequency photon is very high. ($\sim 10^{-6}$). With a practical density of excited Rydberg levels, ($\sim 10^6$) a probability of absorption approaching 1 is possible. Consequently, a microwave energy photon at $2.11 \times 10^{10} H_z$ effects a transition from the one Rydberg level at $16d$ to a neighboring Rydberg level at $16f$ with high probability.

Atoms at the $16f$ level may decay along different paths, one of which paths includes a drop from the $16f$ level to the $3d$ level. As seen in FIG. 2, an optical photon at 8440 A is produced by such spontaneous emission. The wavelength produced by this transition is unique to the $16f$ level which level, in turn, can only be reached by the absorption of the microwave photon at $2.11 \times 10^{10}$ $H_z$ in the illustrated arrangement. Since the branching ratio for the $16f$ level to decay by this radiation is nearly 0.5, it will be understood that an optical photon is produced with high efficiency (approximately 50%) by the absorption of the much lower energy microwave photon. Energy at 8440 A is prevented from entering the interaction chamber, and the 8440 A radiation is detected by the photomultiplier with high efficiency through the filter 38 which discriminates against all other radiative transitions. The optical photon for detection by the photomultiplier is anywhere from approximately 100 to 10,000 more energetic than the microwave or infrared radiation detected to provide, in effect an unconverter. Resolution on the order of 2 - $MH_z$ or one part in $10^5$ of the observation frequency in the microwave and infrared range, respectively, are possible which further distinguishes the invention over prior art arrangements.

With the lasers operating at given frequencies, tuning of the novel photon detector over a relatively narrow band is possible by use of magnetic field coils 44 supplied with direct current from an adjustable DC source 46. Splitting of the Rydberg energy levels by the resultant applied magnetic field (the Zeeman effect) permits tuning at about 2 $MH_z$/gauss. Magnetic fields up to $10^4$ gauss are easily achieved, and fields of $10^5$ gauss are readily possible with small superconducting solenoids for tuning over a range of approximately $10^4$ to $10^5$ $MH_z$. Alternatively, tuning by use of an adjustable electric field in the interaction chamber is possible. The Stark shift for atoms in the Rydberg levels is large since the polarizability scales as $n^7$, and substantial shifts in the level with fields of only several tens of volts/cm are possible. However, care must be taken to avoid mixing of components of neighboring levels which produce radiation at the observation wavelength.

The invention having been described in detail in accordance with the requirements of the Patent Statutes, various changes and modifications will suggest themselves to those skilled in the art. As noted above, resonant excitation of the vaporized material to the desired first Rydberg energy level may be effected by means other than the illustrated two photon system illustrated. Also, as illustrated in Table 3, different high energy level states may be used in the practice of this invention for detection of different energy photons in the low energy electromagnetic range. Also, it will be apparent that other material, such as other alkalis, alkaline earth or metallic atoms, may be employed instead of sodium in the operation of the photon detector. In addition, pulse operation instead of the illustrated continuous operating mode is possible. With the proper selection of materials, operating frequencies, and tuning, operation for photon detection substantially anywhere within a wide low energy band in the microwave and infrared spectrums is possible.

Simultaneous operation over a frequency range by use of a spatially inhomogeneous magnetic field also is contemplated as shown in FIG. 3 to which figure reference now is made. In this embodiment the general arrangement of the atomic source, interaction chambers, lasers, and adjustable D.C. source may be the same as that described with respect to the embodiment shown in FIG. 1, and corresponding elements of the FIG. 1 and FIG. 3 embodiments are provided with the same reference characters. A primary difference in the embodiments resides in the fact that the embodiment of FIG. 3 includes means for supplying the interaction chamber 10 with a spatially inhomogeneous magnetic field. In the arrangement illustrated in FIG. 3 such a magnetic field is provided by use of a field coil 52 which is supplied with direct current from the adjustable D.C. source 46. The coil is formed with a varying number of turns per unit length thereof along the coil axis for the establishment of a magnetic flux field within the interaction chamber 10 which, consequently, varies along the chamber. The use of such coils for the production of spatially inhomogeneous magnetic fields is well known. Other means for the establishment of inhomogeneous magnetic fields are known including, for example, the use of a magnet having non-parallel pole pieces. The invention, obviously, is not limited to use of any particular means for supplying the spatially inhomogeneous magnetic field.

The displacement of components produced by splitting of the Rydberg energy levels is proportional to the magnetic field intensity. Consequently, with the FIG. 3 arrangement, wherein the magnetic field varies along the chamber, the chamber is tuned for a range of low energy radiation to be detected. For purposes of illustration, the interaction chamber is shown supplied with low energy radiation to be detected within the microwave region, by use of an antenna 54 and waveguide 56. Also, a bandpass filter 38A is provided for passage of a range of frequencies from the interaction chamber to an image intensifier 36A. The output from the image intensifier 36A is shown supplied to a vidicon 40A, and the video signal from the vidicon is supplied to any suitable utilization device 60 for display or other use of the vidicon output.

In a modified form of the FIG. 3 arrangement, shown in FIG. 3A, a channel plate photomultiplier 36B is shown in lieu of the image intensifier 36A and vidicon 40A for the direct sensing of the different frequency outputs from the photon filter 38A, and for connection of the filter output to the utilization circuit 60. In other respects the arrangement of FIG. 3A is the same as that shown in FIG. 3. It is intended that the above and other such modifications shall fall within the spirit and scope of the invention as defined in the appended claims.

We claim:

1. A photon detection method for low energy radiation, in the microwave and infrared range, comprising the steps of:
    exciting atoms of a material in the vapor state to a selected first Rydberg energy level without excitation of other atoms thereof to a given second Rydberg energy level,
    exposing said material at the selected first Rydberg energy level to low energy radiation to be detected for allowed electric dipole transition from said selected first Rydberg energy level to said given second Rydberg energy level, and
    detecting radiation produced by spontaneous emission as a result of radiative transition from said second Rydberg energy level to a lower energy level along a given decay path.

2. The photon detection method as defined in claim 1 wherein said detecting step includes detecting only higher energy photons of unique frequency for the method which are produced as a result of said spontaneous emission from said second Rydberg energy level transition to a lower energy level along said given decay path.

3. The photon detection method as defined in claim 1 wherein said radiation produced by spontaneous emission as a result of radiative transition from said second Rydberg energy level to a lower level along a given decay path comprises optical photons which are from 100 to 1,000,000 more energetic than said low energy radiation to be detected.

4. The photon detection method as defined in claim 1 which includes,
    tuning for the detection of a selected frequency of low energy radiation to be detected by control of the allowed electric dipole transition between said first and second Rydberg energy levels.

5. The photon detection method as defined in claim 4 wherein said tuning is effected by application of a magnetic field of selected strength to said highly energized atoms for Zeeman splitting of the first and second Rydberg energy levels.

6. The photon detection method as defined in claim 1 wherein atoms are excited to said selected first Rydberg energy level by resonant excitation by exposure to laser illumination.

7. The photon detection method as defined in claim 1 wherein the allowed electric dipole transition produced by exposure of said atoms at the first Rydberg energy level to radiation to be detected comprises a change in the angular momentum of said atoms without change in the principal quantum number thereof.

8. The photon detection method as defined in claim 1 wherein the allowed electric dipole transition produced by exposure of said atoms at the first Rydberg energy level to radiation to be detected comprises a change in the principal quantum number thereof.

9. The photon detection method as defined in claim 1 which includes,
applying a spatially inhomogeneous magnetic field to said highly energized atoms for a range of Zeeman splitting of the first and second Rydberg energy levels for detection over a range of low energy radiation frequencies.

10. The photon detection method as defined in claim 9 wherein the radiation produced by said spontaneous emission is detected by use of a vidicon.

11. The photon detection method as defined in claim 9 wherein the radiation produced by said spontaneous emission is detected by use of a channel plate photomultiplier.

12. Apparatus for detecting photons in the microwave or infrared region of the electromagnetic spectrum, comprising,
an interaction chamber,
means for providing atoms of a material in the vapor state within said chamber,
means for exciting said atoms to a first Rydberg energy level without excitation to a selected second Rydberg energy level,
means for exposing said excited atoms to photons to be detected for energization of said excited atoms to said second Rydberg energy level from which decay of at least some atoms proceeds along a path which includes a radiative transition of unique wavelength and greater energy than said photons to be detected, and
means for sensing photons of said unique wavelength produced by said radiative transition as a measure of the radiation to be detected.

13. Apparatus for detecting photons as defined in claim 12 including filter means for passing said unique wavelength photons from said interaction chamber to said photon sensing means and discriminating against other radiative transitions within the interaction chamber.

14. Apparatus for detecting photons as defined in claim 12 wherein said means for exciting atoms to said first Rydberg energy level includes laser means for resonant excitation of said atoms without excitation to said selected second Rydberg energy level.

15. Apparatus for detecting photons as defined in claim 12 including,
optical filter means for passing energy within a narrow band including said photons of unique wavelength while absorbing energy outside of said band, and
wherein said sensing means comprises a photomultiplier responsive to energy from said optical filter means to provide an output related to the level of said photons to be detected.

16. Apparatus for detecting photons as defined in claim 12 including,
means for exposing the atoms within the interaction chamber to a spatially inhomogeneous magnetic field for different Zeeman splitting of the first and second Rydberg energy levels along said interaction chamber,
filter means for passing energy within a band of unique wavelength photons from said interaction chamber to said photon sensing means and discriminating against other radiative transitions within the interaction chamber, and wherein,
said photon sensing means includes means for sensing the band of unique wavelength photons passed by said filter means.

17. Apparatus for detecting photons as defined in claim 16 wherein said photon sensing means comprises a vidicon.

18. Apparatus for detecting photons as defined in claim 16 wherein said photon sensing means comprises a channel plate photomultiplier.

19. Apparatus for detecting photons as defined in claim 12 including means for producing a unidirectional magnetic field within the interaction chamber for Zeeman splitting of the first and second Rydberg energy levels.

20. Apparatus for detecting photons as defined in claim 19 wherein a spatially inhomogeneous unidirectional magnetic field is produced by said magnetic field producing means for different Zeeman splitting spatially within the interaction chamber.

* * * * *